United States Patent
Stiepan et al.

(10) Patent No.: US 10,509,330 B2
(45) Date of Patent: Dec. 17, 2019

(54) METHOD AND DEVICE FOR CHARACTERIZING A WAFER PATTERNED USING AT LEAST ONE LITHOGRAPHY STEP

(71) Applicant: Carl Zeiss SMT GmbH, Oberkochen (DE)

(72) Inventors: Hans-Michael Stiepan, Aalen (DE); Andy Zott, Gerstetten (DE); Ulrich Mantz, Schelklingen (DE)

(73) Assignee: Carl Zeiss SMT GmbH, Oberkochen (DE)

( * ) Notice: Subject to any disclaimer, the term of this patent is extended or adjusted under 35 U.S.C. 154(b) by 22 days.

(21) Appl. No.: 15/918,187

(22) Filed: Mar. 12, 2018

(65) Prior Publication Data

US 2018/0203369 A1    Jul. 19, 2018

Related U.S. Application Data

(63) Continuation of application No. PCT/EP2016/075701, filed on Oct. 25, 2016.

(30) Foreign Application Priority Data

Nov. 5, 2015 (DE) .......................... 10 2015 221 772
Jul. 28, 2016 (DE) .......................... 10 2016 213 925

(51) Int. Cl.
*G03F 7/20* (2006.01)
*G01N 21/47* (2006.01)
*G01N 21/95* (2006.01)

(52) U.S. Cl.
CPC ..... *G03F 7/70625* (2013.01); *G01N 21/4788* (2013.01); *G01N 21/9501* (2013.01);
(Continued)

(58) Field of Classification Search
CPC ............ G03F 7/70625; G03F 7/70508; G03F 7/70633; G01N 21/9501; G01N 21/4788;
(Continued)

(56) References Cited

U.S. PATENT DOCUMENTS 6,862,491 B2  3/2005 Levin et al.
7,352,453 B2  4/2008 Mieher et al.
(Continued)

FOREIGN PATENT DOCUMENTS

DE   10 2015 207 002   10/2016
WO   WO 2017/076690     5/2017

OTHER PUBLICATIONS

Thomas A. Germer et al.: Developing an uncertainty analysis for optical scatterometry Metrology, Inspection, and Process Control for Microlithography XXIII, J.A. Allgair, Ed., Proc. SPIE 7272, (2009), 11 pages.
(Continued)

*Primary Examiner* — Dominic J Bologna
(74) *Attorney, Agent, or Firm* — Fish & Richardson P.C.

(57) ABSTRACT

In an aspect, a plurality of parameters characteristic of the patterned wafer are determined based on measurements of the intensity of electromagnetic radiation after the diffraction thereof at the patterned wafer. The intensity measurements are carried out for at least one used structure and at least one auxiliary structure. The parameters are determined based on intensity values measured during the intensity measurements for respectively different combinations of wavelength, polarization and/or order of diffraction, and also on the basis of correspondingly calculated intensity values, with a mathematical optimization method being applied.

20 Claims, 10 Drawing Sheets

(52) U.S. Cl.
CPC ...... *G03F 7/70508* (2013.01); *G03F 7/70633* (2013.01); *G01N 2021/4735* (2013.01); *G01N 2021/4792* (2013.01)

(58) Field of Classification Search
CPC ... G01N 2021/4735; G01N 2021/4792; G01B 2210/56
See application file for complete search history.

(56) References Cited

U.S. PATENT DOCUMENTS

| | | |
|---|---|---|
| 7,916,286 B2 | 3/2011 | Sali et al. |
| 8,339,595 B2 | 12/2012 | Den Boef |
| 8,670,118 B2 | 3/2014 | Den Boef |
| 2003/0091911 A1* | 5/2003 | Noelscher ................ G03F 1/30 430/5 |
| 2003/0219153 A1 | 11/2003 | Levin et al. |
| 2003/0223630 A1 | 12/2003 | Adel et al. |
| 2004/0017574 A1 | 1/2004 | Vuong et al. |
| 2006/0274325 A1 | 12/2006 | Hetzler et al. |
| 2008/0106728 A1 | 5/2008 | Vuong et al. |
| 2008/0117434 A1 | 5/2008 | Verstappen et al. |
| 2009/0037134 A1 | 2/2009 | Kulkarni et al. |
| 2012/0224176 A1 | 9/2012 | Hammond |
| 2013/0116978 A1* | 5/2013 | Yoo ...................... G03F 7/70683 702/189 |
| 2015/0176985 A1 | 6/2015 | Shchegrov et al. |

OTHER PUBLICATIONS

International Search Report for corresponding Appl. No. PCT/EP2016/075701, dated May 18, 2017, 2 pages.

Zhang et al., "Improving optical measurement uncertainty with combined multitool metrology using a Bayesian approach," *Appl Opt.*, 2012;51(25):6196-206.

German Office Action for App. Ser. No. DE 10 2015 221 772.8, dated Jul. 19, 2016 (with English translation), 10 pages.

International Preliminary Report on Patentability, with translation thereof, for corresponding Appl. No. PCT/EP2016/075701, dated May 17, 2018.

* cited by examiner

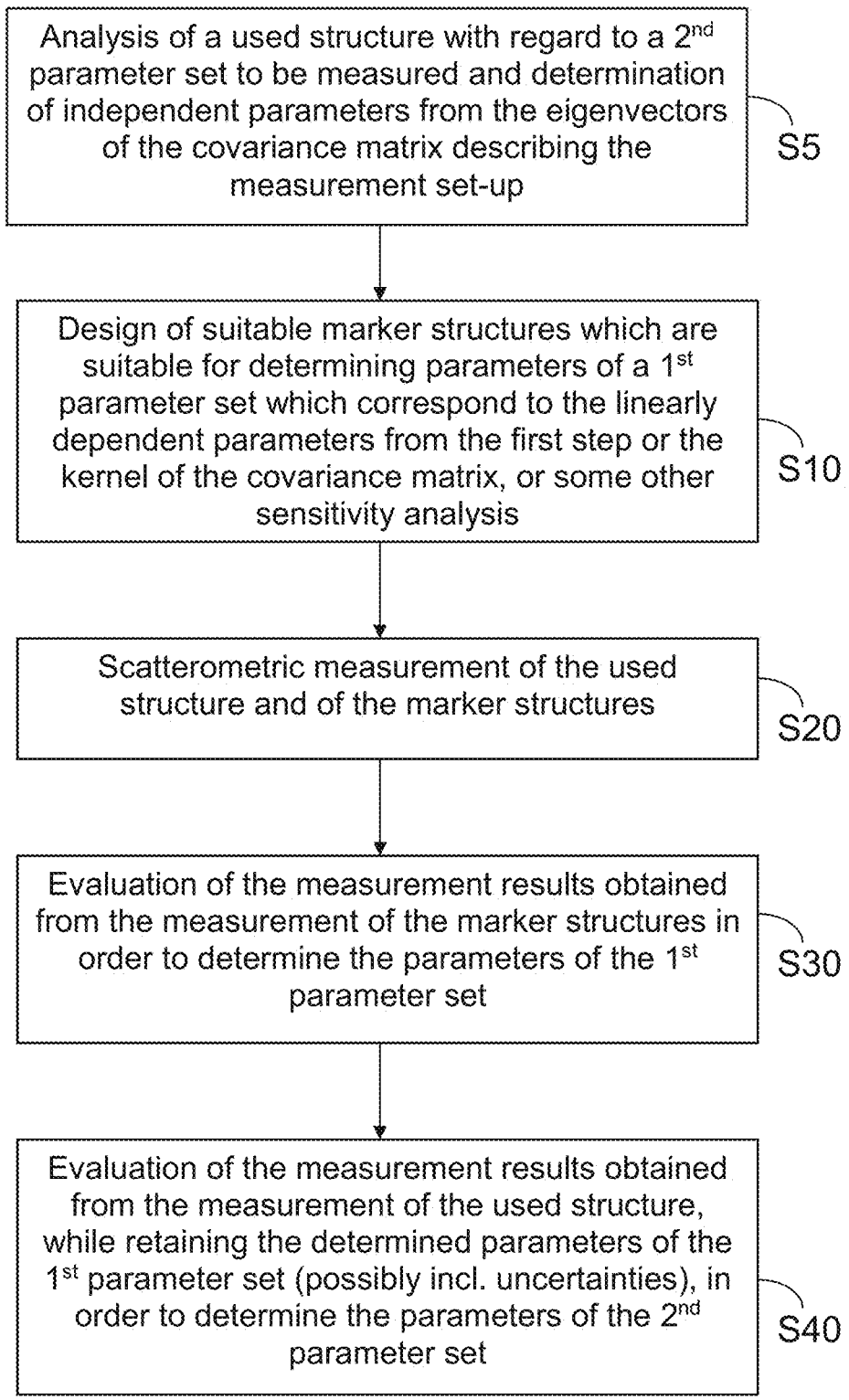

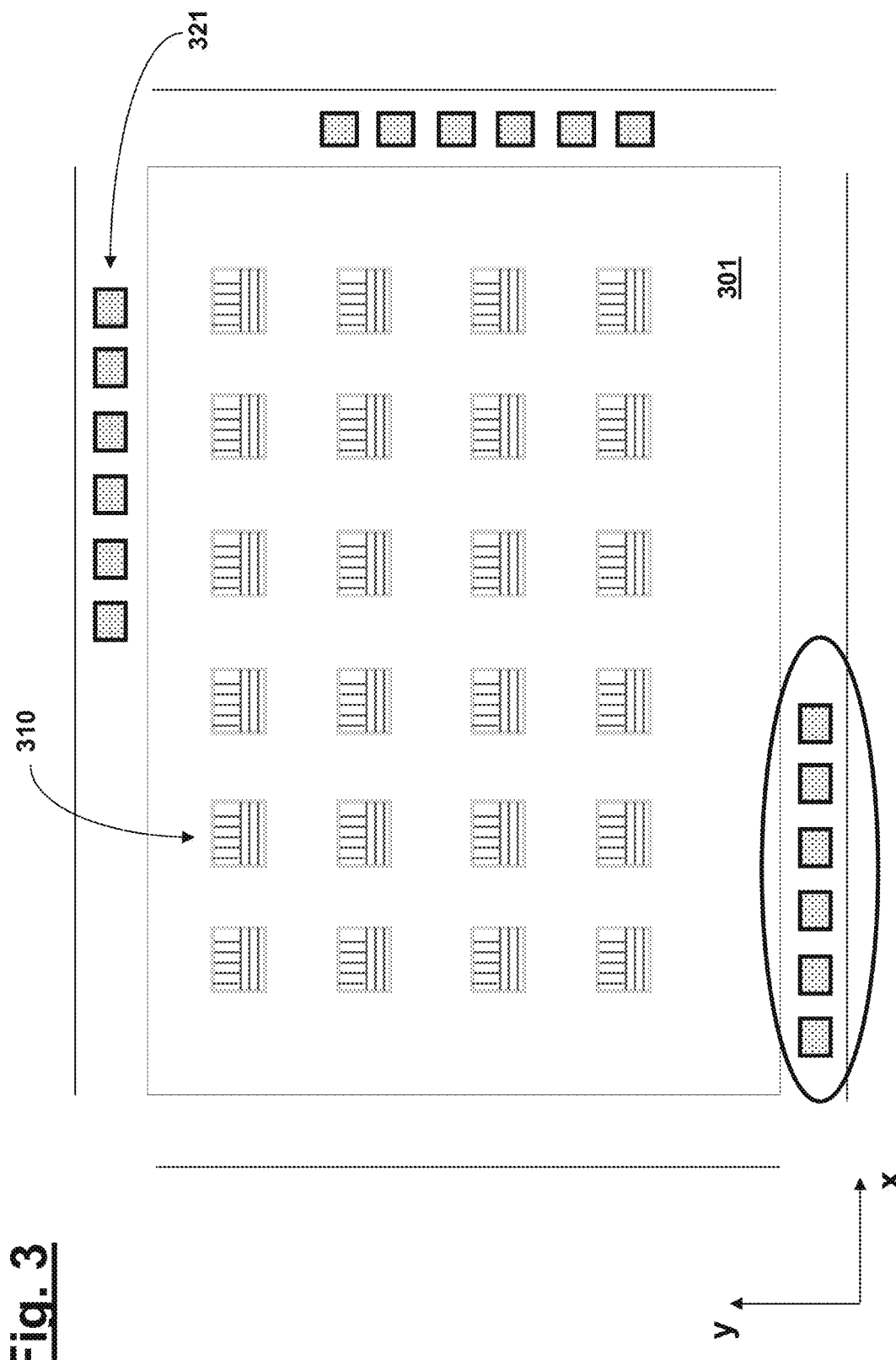

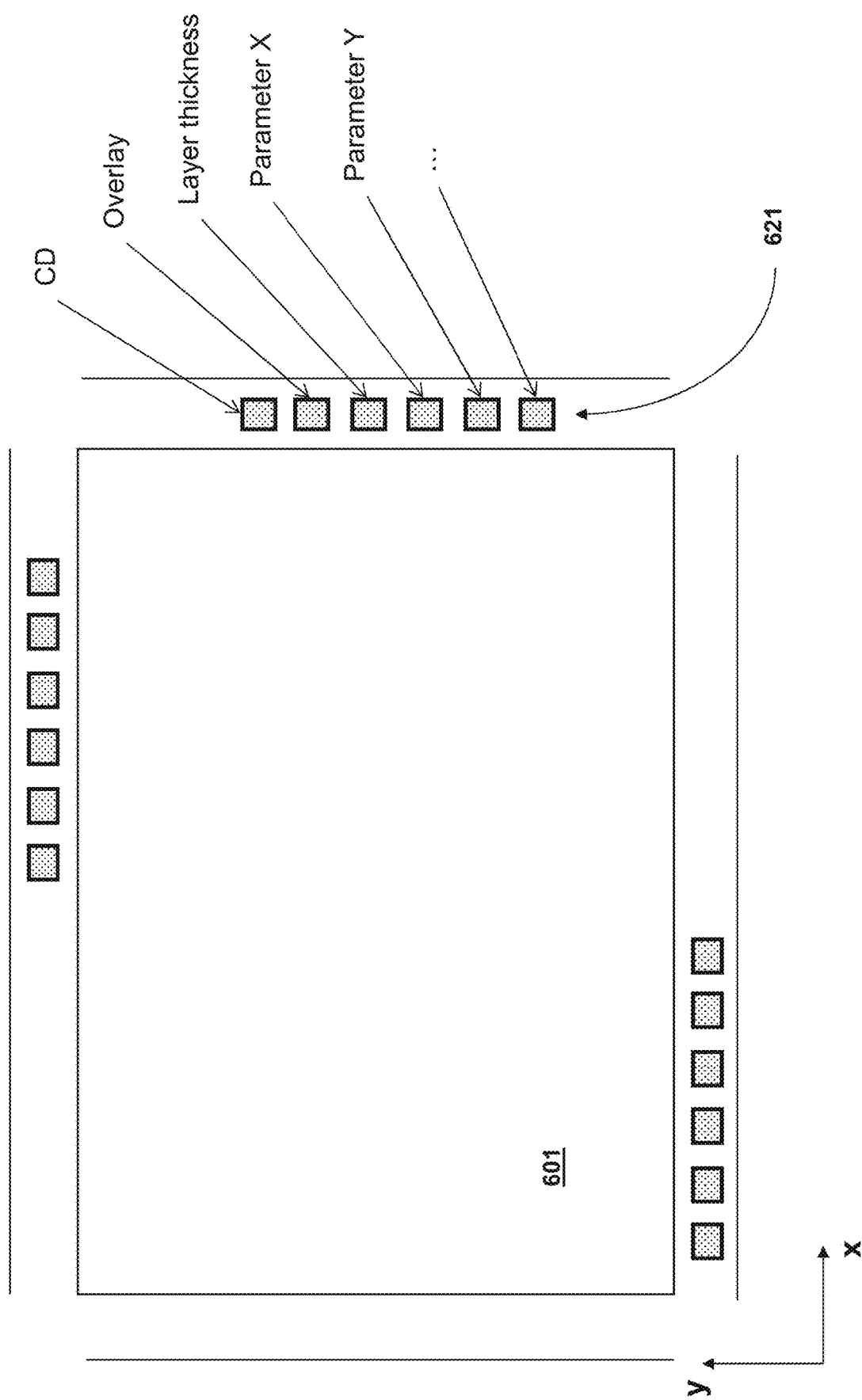

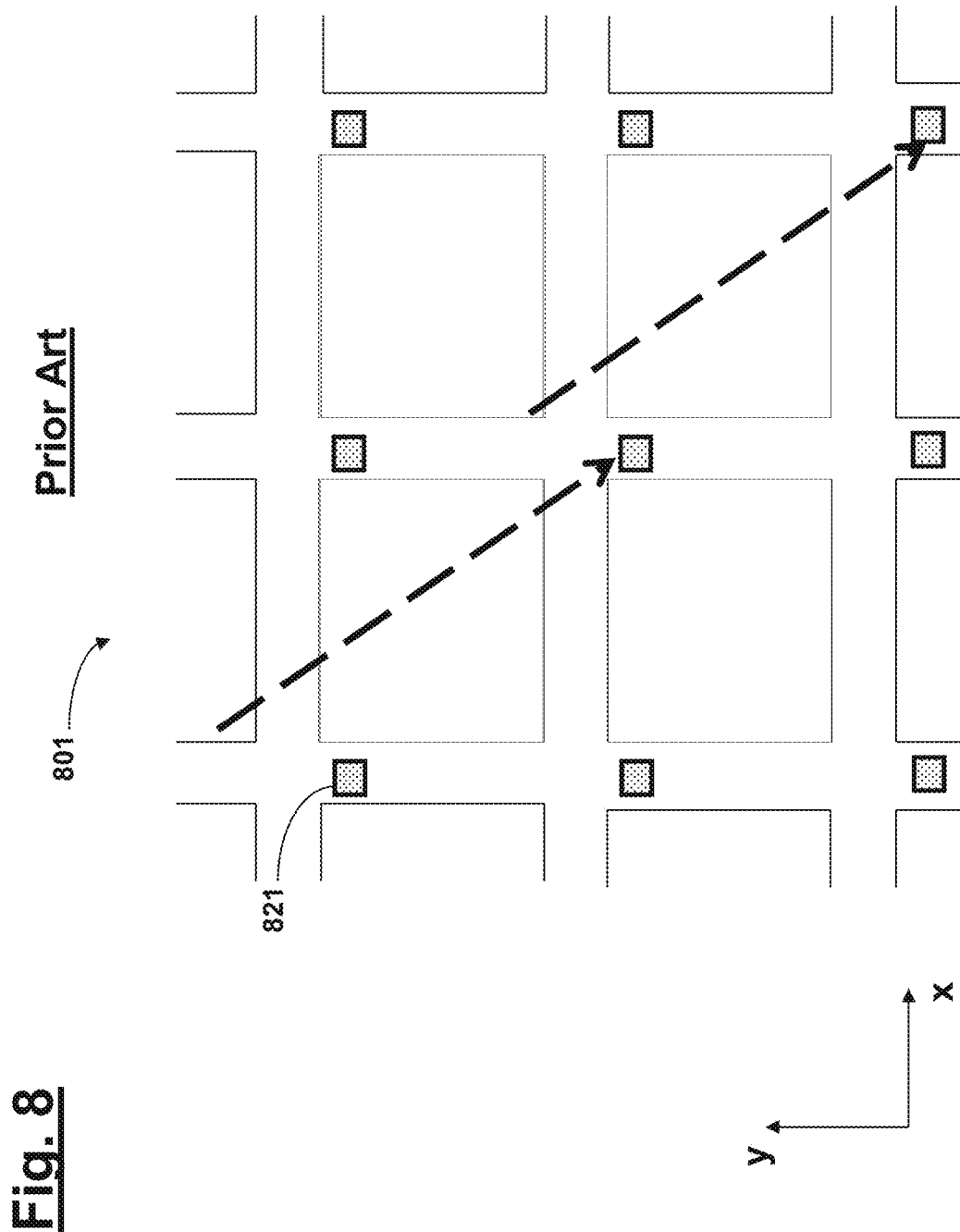

METHOD AND DEVICE FOR CHARACTERIZING A WAFER PATTERNED USING AT LEAST ONE LITHOGRAPHY STEP

CROSS-REFERENCE TO RELATED APPLICATIONS

The present application is a continuation of, and claims benefit under 35 USC 120 to, international application PCT/EP2016/075701, filed Oct. 25, 2016, which claims benefit under 35 USC 119 of the German patent application DE 10 2015 221 772.8, filed on Nov. 5, 2015, and of the German patent application DE 10 2016 213 925.8, filed on Jul. 28, 2016. The entire disclosure of these applications are incorporated by reference herein

FIELD

The disclosure relates to a method and a device for characterizing a wafer patterned using at least one lithography step.

BACKGROUND

Microlithography is used for producing microstructured components such as, for example, integrated circuits or LCDs. The microlithography process is carried out in what is called a projection exposure apparatus, which includes an illumination device and a projection lens. The image of a mask (=reticle) illuminated by way of the illumination device is in this case projected by way of the projection lens onto a substrate (e.g. a silicon wafer) coated with a light-sensitive layer (photoresist) and arranged in the image plane of the projection lens, in order to transfer the mask structure to the light-sensitive coating of the substrate.

In this case, in practice there is a desire to monitor parameters characteristic of the patterned wafer, e.g. the CD value or the layer thickness. Particularly in so-called "multi-patterning" methods for undershooting the resolution limit of the optical system with structures produced on the wafer in a plurality of lithography steps, a large number of process parameters have to be monitored. The so-called overlay is often of particular importance here.

When determining such parameters it is known, inter alia, to produce auxiliary structures in the form of suitable marker regions in particular in edge regions of the wafer elements respectively produced, in order to carry out, on the basis of the auxiliary structures, a diffraction based determination of the respective relevant parameters in a scatterometric setup.

One issue that occurs in practice here is that the parameter values determined on the basis of such auxiliary structures do not necessarily represent the actual behavior of the used structures contained on the wafer, which may be attributable e.g. to an inadequate correlation between used structure and auxiliary structure and/or a large distance between these structures. A further issue that occurs in practice results occasionally from the comparatively high number of auxiliary structures involved, the progressive evaluation of which would be accompanied by a significant impediment of the throughput of the lithography method.

Furthermore, the determination of a plurality of relevant parameters within a used structure of possibly complex construction on a wafer also poses a demanding challenge insofar as the relevant parameters, under certain circumstances, can be determined simultaneously in a single measurement setup only with difficulty. This is the case if the parameters are linearly dependent in the sense that certain combinations of these values lie in the kernel (i.e. eigenvectors with respect to the eigen-value 0) of the covariance matrix describing the issue. This case often occurs in the event of a deviation between measured and simulated values that is detected in a diffraction based determination, with the result that it is not possible to decide un-ambiguously what parameter variation causes the deviation.

With respect to the prior art, reference is made merely by way of example to US 2006/0274325 A1, U.S. Pat. No. 8,339,595 B2, U.S. Pat. No. 8,670,118 B2 and US 2012/0224176 A1, US 2003/0219153 A1, US 2009/0037134 A1 and U.S. Pat. No. 7,916,286 B2.

SUMMARY

The disclosure seeks to provide a method and a device for characterizing a wafer patterned using at least one lithography step which allow one or more characteristic variables characteristic of the patterned wafer to be determined as rapidly and reliably as possible with the least possible impediment of the throughput of the projection exposure apparatus.

In accordance with one aspect, in the case of a method according to the disclosure for characterizing a wafer patterned using at least one lithography step, a plurality of parameters characteristic of the patterned wafer are determined on the basis of measurements of the intensity of electromagnetic radiation after the diffraction thereof at the patterned wafer, wherein these intensity measurements are carried out for at least one used structure and at least one auxiliary structure, and wherein the parameters are determined on the basis of intensity values measured during the intensity measurements for respectively different combinations of wavelength, polarization and/or order of diffraction, and also on the basis of correspondingly calculated intensity values, with a mathematical optimization method being applied.

The determination of the parameters characteristic of the patterned wafer includes the following steps:
  determining parameters of a first parameter set on the basis of the intensity values obtained for the at least one auxiliary structure; and
  determining parameters of a second parameter set taking account of the determined parameters of the first parameter set.

The disclosure is based on the concept, in particular, in the case of the parameters characteristic of a patterned wafer that are respectively to be determined, of differentiating between two different parameter sets with regard to the evaluation of the intensity measurements carried out in a scatterometric setup insofar as, in a two stage evaluation, firstly only the intensity measurements carried out on one or more auxiliary structures are evaluated and used for determining a first parameter set. The parameters of the first parameter set that are evaluated in such a way on the basis of the at least one auxiliary structure are then subsequently correspondingly pre-defined for the remaining parameters of the second parameter set (if appropriate taking account of suitable uncertainties or a respectively predefined variation interval), such that as a result all parameters—both those of the first parameter set and those of the second parameter set—can be determined even in the case of a comparatively complex wafer patterning.

By virtue of the fact that, according to the disclosure, in the two stage evaluation described above, firstly only specific parameters are calculated on the basis of one or more suitable auxiliary structures, the disclosure makes it possible to differentiate between parameters that are readily determinable on the basis of the measurement of auxiliary structures and other parameters that are comparatively more difficult to determine—for instance owing to an existing dependence on the parameters—and to use the information obtained from the first stage of the abovementioned evaluation during the subsequent determination of the respective parameters of the second parameter set (which are typically the parameters that are comparatively more difficult to determine). By way of example, the first parameter set can be assigned such parameters which vary comparatively little across the wafer and/or whose properties upon determination at the auxiliary structures differ only comparatively little from those upon determination at the used structures.

Proceeding from this concept, the disclosure includes the further principle of configuring the relevant auxiliary structures on the wafer in a targeted manner from the outset (i.e. before the abovementioned intensity measurements are actually carried out) in such a way that the auxiliary structures are suitable or optimized precisely for the determination of the relevant parameters of the first parameter set.

This targeted configuration of the auxiliary structures can be effected in each case on the basis of a sensitivity analysis in which the sensitivity of different auxiliary structures is assessed for a diffraction based determination of a respective one of the parameters of the first parameter set. In this respect, reference is made to Thomas A. Germer et al.: "Developing an uncertainty analysis for optical scatterometry Metrology, Inspection, and Process Control for Microlithography XXIII, J. A. Allgair, Ed., Proc. SPIE 7272, (2009).

In accordance with one embodiment, the intensity measurements are carried out simultaneously for the at least one used structure and the at least one auxiliary structure for a respective combination of wavelength, polarization and/or order of diffraction. In other words, the diffraction based measurement according to the disclosure for a specific measurement time or measurement step is not just effected for one region on the wafer, rather a plurality of regions or structures on the wafer are measured simultaneously, such that even a measurement of a multiplicity of used and/or auxiliary structures that is involved for characterizing complex used structures is made possible without significant impediment of the throughput of the projection exposure apparatus.

In accordance with one embodiment, the intensity measurements are carried out for a plurality of auxiliary structures, the intensity measurements being carried out simultaneously for a respective combination of wavelength, polarization and/or order of diffraction. In this case, determining parameters of the first parameter set on the basis of the intensity values obtained for the auxiliary structures can include a comparison of the intensity values with intensity values stored in at least one database, wherein in the database an associated intensity spectrum is respectively assigned to a plurality of auxiliary structures. A localization of structures respectively suitable for determining a parameter on the wafer can be effected on the basis of the comparison with intensity values stored in the at least one database.

In accordance with this aspect, the disclosure includes the further concept of deciding, already on the basis of the intensity measurements carried out, where on the wafer the structures relevant in each case for the evaluation of specific parameters are arranged, with the result that a corresponding prior input of this information is unnecessary. Rather, according to the disclosure, it is possible to carry out directly a scatterometric recording of a larger field on the wafer, since the relevant information about the position of the relevant structures to be measured is supplied from the measured data and the comparison thereof with a previously provided database itself.

In other words, according to the disclosure, firstly a database having individual typical structures and respectively assigned intensity spectra can be provided, which database contains a characteristic intensity spectrum for each of the relevant structures. A measurement result which is then obtained in the context of the actual diffraction based intensity measurement and which corresponds sufficiently (i.e. within predefinable error limits) well to one of the relevant reference spectra contained in the database then allows the conclusion to be drawn that the structure assigned to the reference spectrum in the database is present in the relevant wafer region and can be used for the respectively suitable parameter determination.

The above-described concept of the database based localization of auxiliary structures on the wafer is also advantageous independently of the above-described approach of a two stage evaluation with differentiation in parameters of the first and second parameter sets.

Therefore, in accordance with a further aspect, the disclosure also relates to a method for characterizing a wafer patterned using at least one lithography step,
wherein at least one parameter characteristic of the patterned wafer is determined on the basis of a plurality of measurements of the intensity of electromagnetic radiation after the diffraction thereof at the patterned wafer;
wherein the at least one parameter is determined on the basis of intensity values measured during these intensity measurements for respectively different combinations of wavelength, polarization and/or order of diffraction, and also on the basis of correspondingly calculated intensity values, with a mathematical optimization method being applied; and
wherein determining the parameters before a mathematical optimization method is applied includes a comparison of intensity values obtained during the intensity measurements with intensity values stored in at least one database, wherein in the database an associated intensity spectrum is respectively assigned to a plurality of structures.

In accordance with one embodiment, a localization of structures respectively suitable for determining a parameter on the wafer is effected on the basis of the comparison with intensity values stored in the at least one database.

In accordance with one embodiment, the parameters characteristic of the patterned wafer include at least one parameter from the group CD value, etching depth and overlay accuracy of two structures produced in different lithography steps.

In accordance with one embodiment, for a partial region of the wafer, a comparison of the intensity values measured for the partial region with intensity values obtained for a reference is carried out.

In accordance with a further aspect, the disclosure also relates to a method for characterizing a wafer patterned using at least one lithography step,
wherein a plurality of parameters characteristic of the patterned wafer are determined on the basis of measurements of the intensity of electromagnetic radiation after the diffraction thereof at the patterned wafer;
wherein the parameters are determined on the basis of intensity values measured during the intensity measurements for respectively different combinations of wavelength, polarization and/or order of diffraction, and also on the basis of correspondingly calculated intensity values; and wherein for a partial region of the wafer, a comparison of the intensity values measured for the partial region with intensity values obtained for a reference is carried out.

In accordance with a further aspect, the disclosure also includes the concept of reducing or even entirely avoiding the outlay associated with creating a database such as is used in the embodiments described above. This firstly takes account of the circumstance that the database calculations mentioned are very time-consuming and, moreover, the relevant databases have to be individually created anew in each case for each design of the wafer structures to be produced.

In order to reduce or avoid this outlay for the database calculation, the disclosure is based, then, on the further consideration that alongside the respectively evaluated marker regions, owing to the intensity measurements that are carried out simultaneously anyway in the context of the disclosure for a larger wafer region or for a multiplicity of spots, corresponding data information is also present for the used regions situated inherently outside the marker regions, and that the data information or regions can likewise be used, as described below. As a result, the disclosure also advantageously makes use of the circumstance that the regions which are situated outside the marker regions and whose intensity data present anyway are now additionally used according to the disclosure indeed still have significant similarities with the actual marker regions. The marker and used regions are typically produced in one step with the same illumination settings in a lithographic step; in this regard, "intra die variations" (="intra chip variations") after the development of the resist can be identified well via this method. Furthermore, the structure sizes used for the markers are often also similar to those used for the surrounding regions, such that effects during etching are readily transferrable from one structure to the other.

Against this background, the approach of deducing possible variations of specific characteristic parameters (e.g. etching depth) from the measurement data or intensity values present for the marker regions (that is to say the "spectral response" of the system) is, with a certain legitimacy, also applicable to measurement data present for regions situated outside the marker regions.

In order then likewise to utilize the measurement data or intensity values present for the regions situated outside the marker regions, according to the disclosure firstly a suitable reference is defined, whereupon—without recourse to a database—a comparison of the measurement data or intensity values obtained for the regions situated outside the marker regions and for the relevant reference is carried out. Merely by way of example, the reference can be a known wafer distinguished by the fact that the measurements already carried out at all marker regions on the wafer have yielded a comparatively good correspondence to the nominal values of the relevant characteristic parameters. In other words, the reference is preferably chosen such that the relevant characteristic parameters of the reference already correspond as exactly as possible to the respective setpoint values.

If the comparison carried out as described above then yields deviations above a respectively defined threshold value (wherein the relevant threshold value, as described in even greater detail below, can be defined on the basis of various criteria), it can be deduced from this that an excessively high deviation of one or more characteristic parameters from the respective nominal values is present. That is to say that specific specified variables such as e.g. the width of a conductor track have been undershot or exceeded and, as a result, e.g. the functionality of the wafer or more precisely of the chip is no longer provided. It is then possible in turn to react to this at an early stage by stopping or by correcting the production process.

In accordance with one embodiment, therefore, the wafer patterning process is stopped or modified if a deviation determined during the comparison exceeds a pre-defined threshold value.

The respective threshold value can be defined, merely by way of example, in such a way that for two wafers, one of which has been deliberately disturbed or impaired with regard to a relevant characteristic parameter, the respective spectral responses of the system are compared with one another and the deviations that can still be tolerated are accordingly defined. In further embodiments, the respective threshold value can be defined on the basis of the average value of the measurement data or intensity values obtained for a multiplicity of wafers (wherein, merely by way of example, twice the value of the standard deviation in the distribution of intensity values thus obtained can be assumed as a still tolerable deviation).

The above-described concept of likewise utilizing the measurement data or intensity values present for the regions situated outside the marker regions, without in this respect having recourse to the databases discussed initially or creating such a database for the relevant region, can furthermore also be used to evaluate regions on the wafer which would not be accessible at all to a database based evaluation in accordance with the embodiments described above (e.g. for lack of a sufficient periodicity of the structures present in the regions).

Furthermore, the described concept of likewise utilizing the measurement data or intensity values present for the regions situated outside the marker regions can, if appropriate, also be combined with the database based embodiments described above. In this regard, for a partial region of the wafer (which has e.g. comparatively complex structures) it is possible to carry out a database based evaluation with the embodiments described above, whereas for other regions it is possible to dispense with such a database based evaluation (by virtue of the fact that there the pure measurement values as described above are compared with those of the previously defined reference).

In accordance with one embodiment, the partial region of the wafer is situated outside periodic used and auxiliary structures present on the wafer, which are evaluated via scatterometry and in a model based manner.

In accordance with one embodiment, the partial region of the wafer is arranged adjacent to a used or auxiliary structure present on the wafer.

The disclosure furthermore relates to a device for characterizing a wafer patterned using at least one lithography step, wherein the device is configured to carry out a method having the features described above. With regard to advantages and advantageous configurations of the device, reference is made to the above explanations in association with the method according to the disclosure.

Further configurations of the disclosure can be gathered from the description and the dependent claims.

BRIEF DESCRIPTION OF THE DRAWINGS

The disclosure is explained in greater detail below on the basis of exemplary embodiments illustrated in the accompanying figures, in which:

FIG. 2 shows a flow diagram for explaining the possible sequence of one embodiment of a method according to the disclosure;

FIGS. 3, 4A, 4B, 5, 6, 7A, 7B, 7C and 7D show schematic illustrations for explaining various embodiments of the disclosure;

FIG. 8 shows a schematic illustration for elucidating an issue addressed by the present disclosure;

DETAILED DESCRIPTION OF THE PREFERRED EMBODIMENTS

Figure 1:
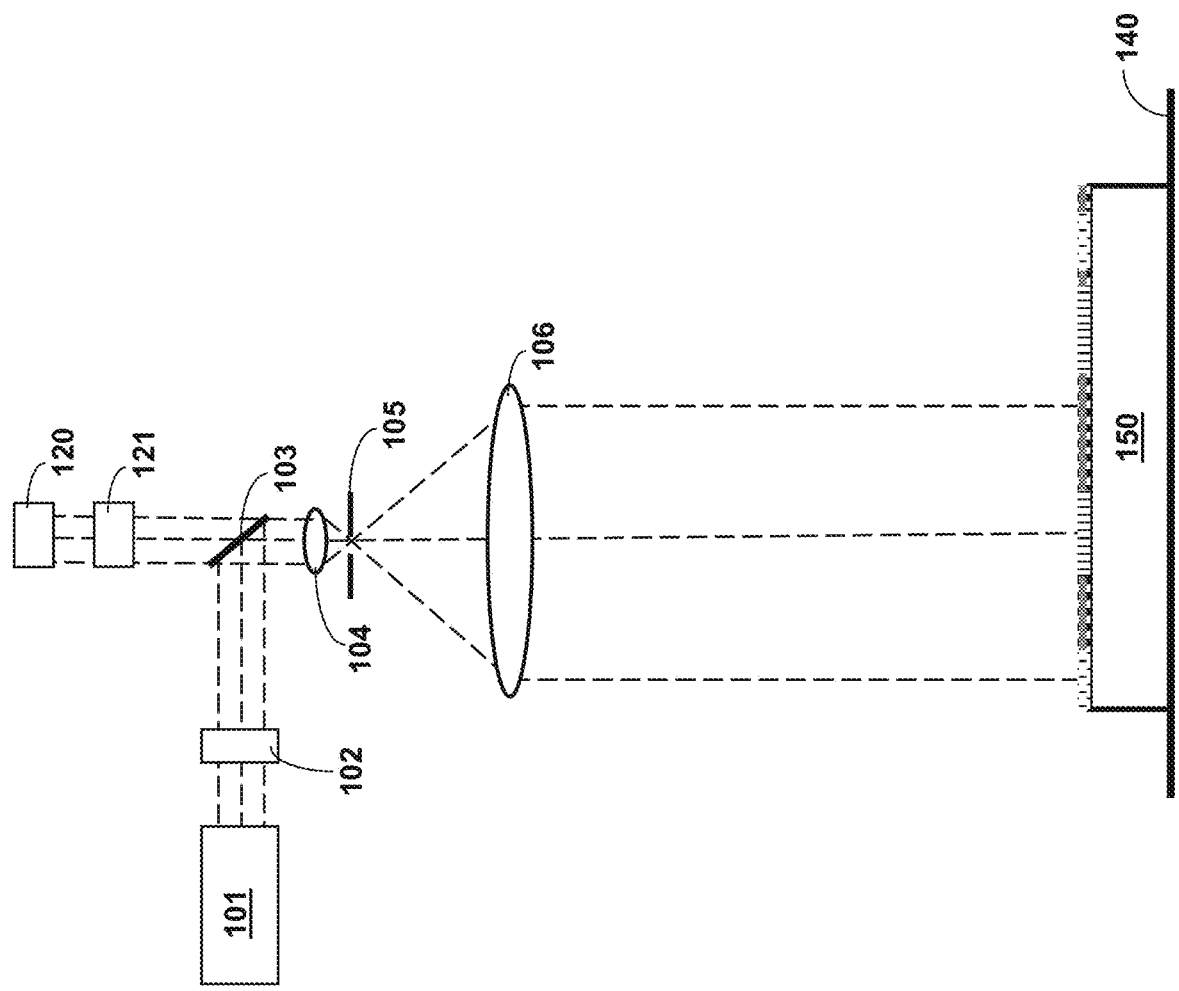
FIG. 1 shows a schematic illustration of the possible setup of a measuring arrangement or device for carrying out the method according to the disclosure.

FIG. 1 firstly shows, in a schematic illustration, the possible setup of a measuring arrangement or device for carrying out the method according to the disclosure.

The measuring arrangement in FIG. 1 is configured as a scatterometer and includes a light source 101, which can be e.g. a tuneable light source for generating a wavelength spectrum (for example in the wavelength range of 300 nm to 800 nm). The light from the light source 101, via a polarizer 102 (possibly exchangeable in order to set linearly polarized light having different polarization directions), a beam splitter 103, a lens element 104, a stop 105 and a further lens element 106, impinges on a wafer 150 arranged on a wafer plane or wafer stage 140, or impinges on the structures (merely indicated schematically in FIG. 1) that have already been produced lithographically on the wafer 150.

After diffraction at the structures, the light in accordance with FIG. 1 passes in the 0 order of diffraction back via an analyzer 121 onto a detector (camera) 120. With the use of different spectral filters or polarizers 102, the intensity measurement can be effected by the detector 120 for a multiplicity of different wavelengths or polarization states. In further embodiments, other orders of diffraction can also be taken into account in addition or as an alternative to the 0 order of diffraction.

On the basis of the intensity values measured by the detector 120, via comparison (in particular difference formation), a determination or monitoring of the relative position of structures produced in different lithography steps on the wafer 150 (e.g. marker structures provided for this purpose) can be performed in principle in a model based fashion in a manner known per se.

In this case, the measurement values obtained for different combinations of wavelength, polarization and order of diffraction (e.g. 2*2*10=40 measurement values in the case of measurement for two different polarization states, two orders of diffraction and ten different wavelengths) are respectively fitted to a model generated by solving Maxwell's equations, wherein e.g. the least square deviation method can be applied. In this case, if appropriate, an iteration can also be carried out, as indicated. In this case, the above-described determination of the values—respectively assigned to a patterned wafer region—of the relevant parameters (e.g. overlay value, CD value, etc.) at each measurement time or in each measurement step is effected not just for a single patterned wafer region, but rather simultaneously for a plurality of wafer regions, i.e. for determining a plurality of values of the respective parameters, wherein each of these values of a parameter is assigned to one of the plurality of regions being measured simultaneously. Accordingly, according to the disclosure, in each measurement step or at each measurement time, not just individual spots (for determining in each case only a single overlay value) are measured, rather a field is imaged onto the relevant detector (camera) 120. In this case, the field imaged according to the disclosure can have a size of typically a plurality of mm$^2$. In this case, merely by way of example, the simultaneously recorded overall region on the wafer can correspond to the size of a typical wafer element or chip ("die") and have a value of e.g. 26 mm*33 mm.

One possible embodiment of the method according to the disclosure is described below with reference to FIGS. 2 to 4.

Figure 4B:
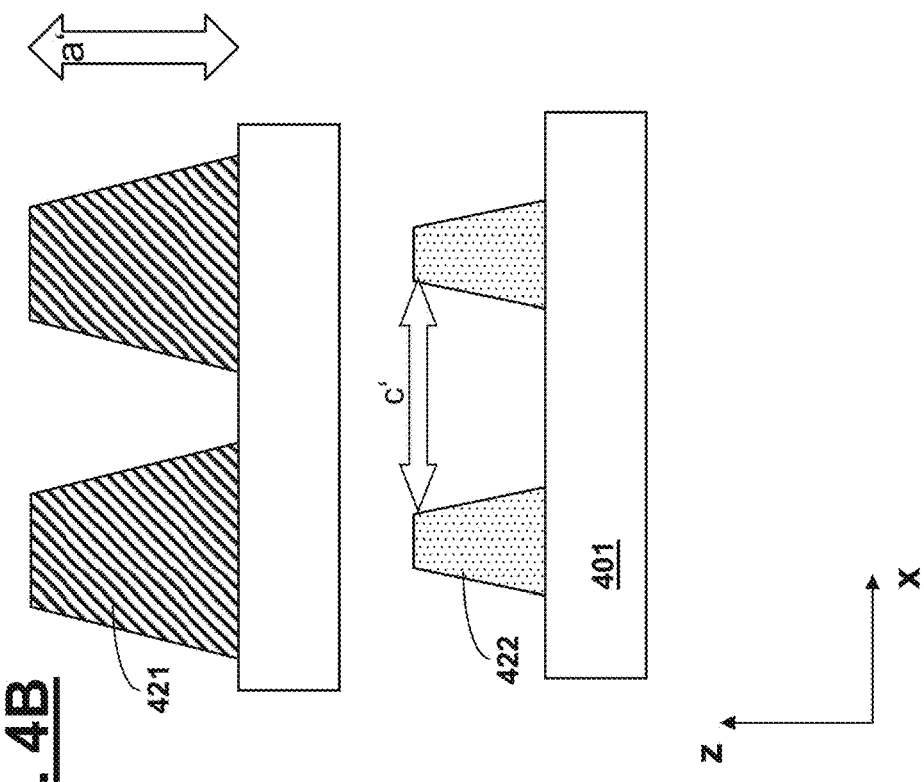
Figure 4A:
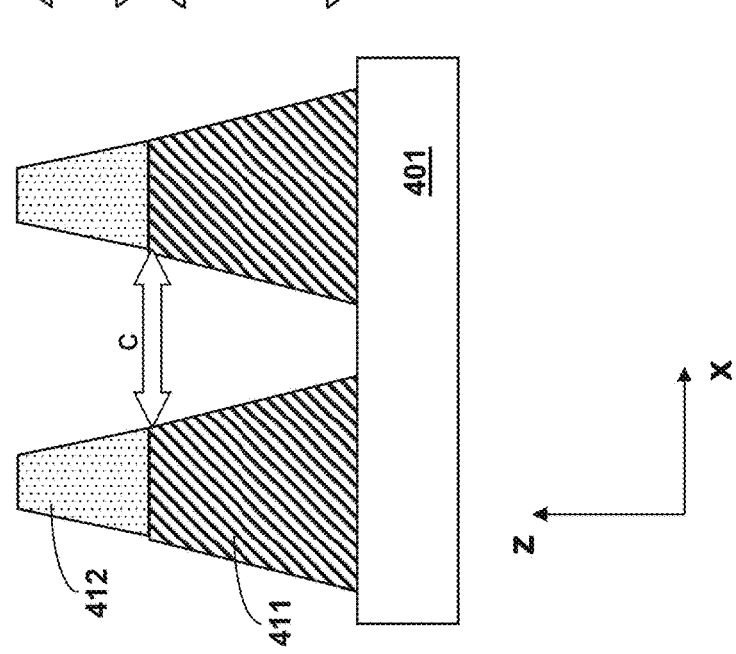

FIG. 3 shows, in a merely schematic and greatly simplified illustration, a wafer 301 in plan view, wherein both diverse used structures 310 and auxiliary structures 321 are situated on the wafer 301, wherein the auxiliary structures 321 mentioned last are typically arranged outside the used structures or "scribe lines" (i.e. breaking lines or regions of the wafer) situated between the chips respectively produced. FIGS. 4A-4B illustrate merely schematically possible parameters for characterizing a patterned wafer, wherein "a" and "b" respectively denote layer thicknesses of two layers 411 and 412, respectively, applied above a substrate 401 in different lithography steps, and wherein "c" denotes the distance between the layer regions produced thereby on the substrate 401 at the transition between the layers 411, 412.

While simultaneously determining all the parameters a, b and c in a wafer patterned in this way is made more difficult, then, since the parameters a, b and c are not independent of one another under certain circumstances, nevertheless it is possible firstly to effect a separate determination both of the parameter a and of the parameter c on the basis of suitable auxiliary structures in accordance with FIG. 4B.

According to the disclosure, therefore, in a two stage evaluation, firstly the determination of the parameters a' and c' is effected, which parameters—as known on account of previous analyses—are directly correlated with a and c, respectively, on the basis of the intensity values obtained for the relevant auxiliary structures and with the above-described optimization method being applied. Determining the parameters a' and c' (corresponding to a first parameter set) is then followed by predefining the values obtained here for a and c (if appropriate with a suitable possible variation interval in each case) for a second evaluation step for determining the parameter b (corresponding to the second parameter set), which can then likewise be determined on the basis of the mathematical optimization method described above and in accordance with the evaluation of the actual used structure in accordance with FIG. 4A.

As has been described above with reference to FIG. 4B, the auxiliary structures used for determining the first parameter set are preferably optimized precisely in a targeted manner to the effect that they are suitable in each case for determining one or more parameters, which can be effected on the basis of a sensitivity analysis. In other words, the auxiliary structures 321 shown in FIG. 3 are preferably configured from the outset on the wafer 301 in such a way that they are respectively optimized for the measurement of specific parameters.

FIG. 2 illustrates the sequence of the above-described method in a flow diagram.

A first step S5 involves carrying out an analysis of the structure to be measured with regard to a second parameter set in respect of which parameters are directly determinable and/or which further parameters have to be implemented via auxiliary structures possibly to be produced.

Accordingly, a further step S10 involves carrying out the suitable design of the auxiliary or marker structures which are suitable for determining the parameters of a first parameter set, which are chosen such that the parameters of the second parameter set that cannot be determined directly can thereby be determined, once again on the basis of a sensitivity analysis.

Figure 5:
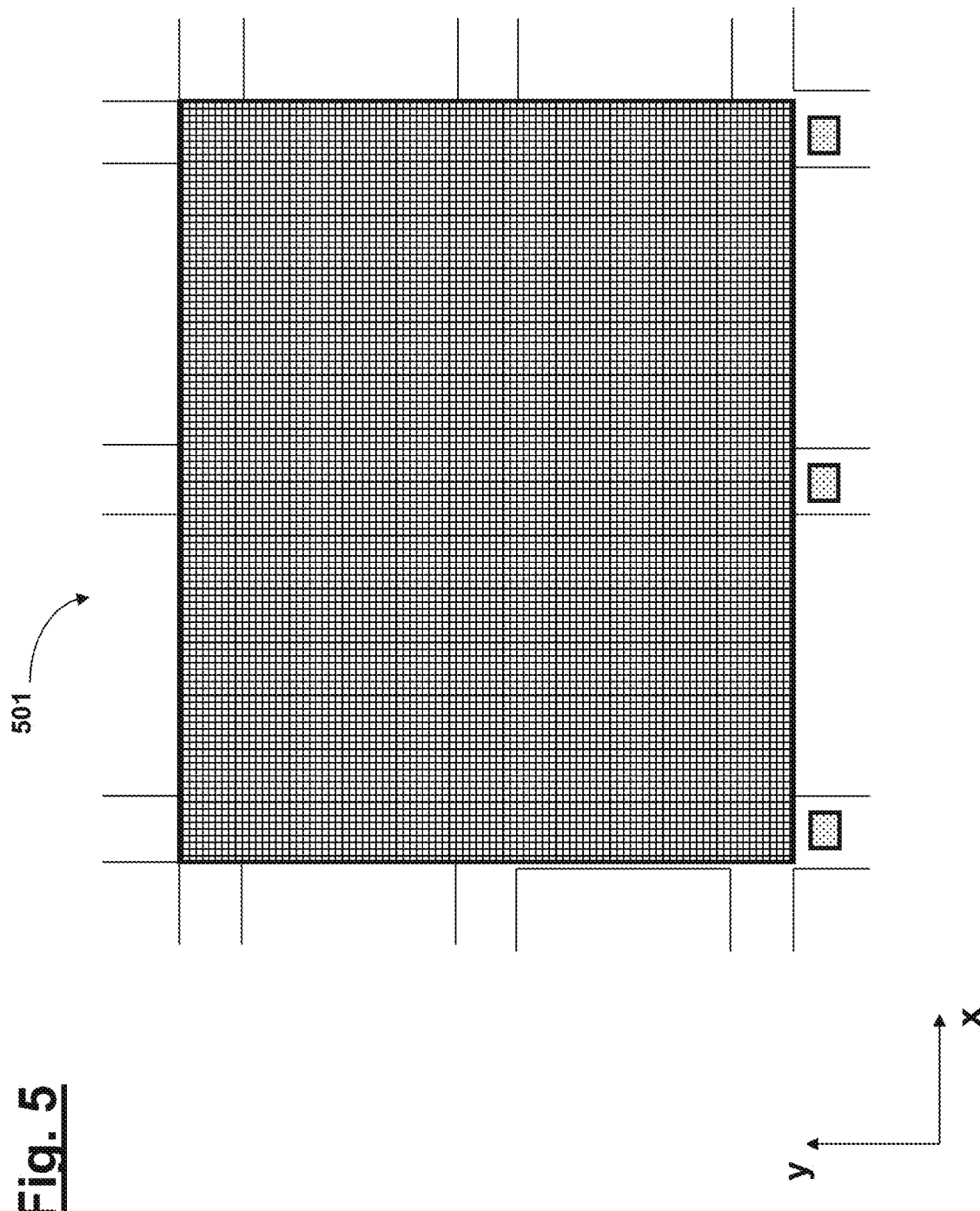

Afterward, a step S20 involves carrying out the diffraction based measurement of the used structures produced on the wafer and also of the auxiliary structures mentioned above. According to the disclosure, these intensity measurements themselves are carried out simultaneously both for the used structures and for the auxiliary structures preferably for each combination of wavelength, polarization and order of diffraction. In other words, instead of progressive illumination and diffraction based measurement of individual auxiliary structures 821 in accordance with FIG. 8, an entire field 501 is illuminated in accordance with FIG. 5, wherein the field, merely by way of example, can have a size of a plurality of $mm^2$, e.g. 30 mm*40 mm. Accordingly, the disclosure also avoids possible alignment steps that are used during the abovementioned progressive illumination and diffraction based measurement of individual auxiliary structures in order to precisely set the measurement position depending on the respective position of the auxiliary structures that are moved to sequentially.

In this case, individual wafer regions (obtained e.g. in accordance with FIG. 5 by division into a multiplicity of individual measurement channels) respectively correspond to a detector region (concomitantly including one or more camera pixels on the detector).

The intensity values obtained are then evaluated in two stages as described above. Firstly, step S30 involves determining a first parameter set on the basis of the measurement results obtained at the auxiliary structures. It is only then in step S40 that the parameters of the second parameter set are determined using the results from step S30 (namely with the values obtained for the parameters of the first parameter set being predefined, if appropriate with deviations being permitted within a variation interval).

As is explained below with reference to FIGS. 6 and 7, on the basis of these intensity values measured simultaneously in each case, it is also possible to localize the (auxiliary) structures to be used in each case for the parameter determination on the wafer. For this purpose, individual typical structures with respectively assigned intensity spectra can be stored from the outset in a database, wherein a comparison of the spectra obtained on the basis of the intensity measurements actually determined with the spectra contained in the relevant database enables in each case the decision as to whether an already known or identified structure is present in the respective wafer region and what structure (or what parameters to be determined on the basis of the structure) is (are) involved here.

Therefore, if the intensity measurements are carried out for example using the arrangement in accordance with FIG. 1 for ten different wavelengths and two polarizations and the database includes twelve pairs each including a typical (auxiliary) structure and a respectively associated, wavelength dependent intensity spectrum, on the basis of a comparison of the vector including the 10*2 intensity values with the twelve spectra of the database a decision is taken as to whether an already known or identified structure is present in the respective wafer region and what structure (or what parameter to be determined on the basis of the structure) is involved here.

Figure 7A:
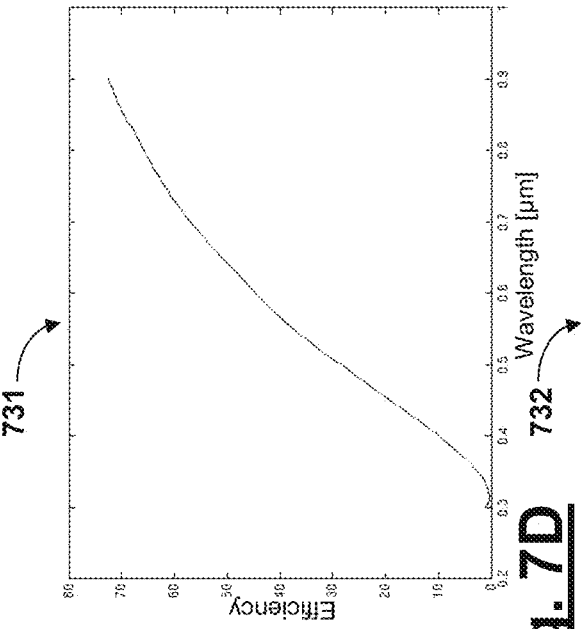
Figure 7B:
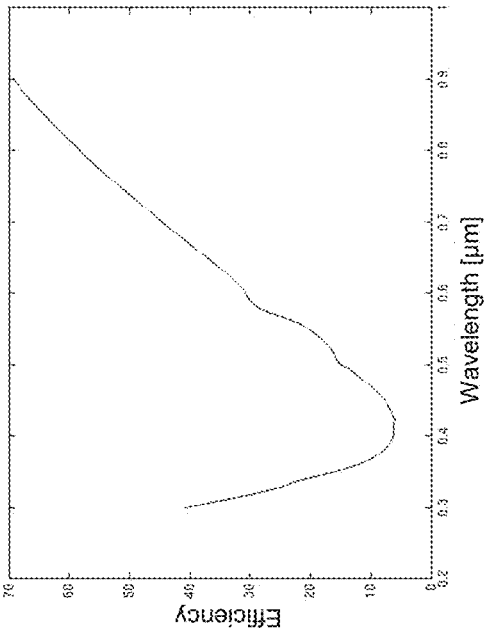
Figure 7C:
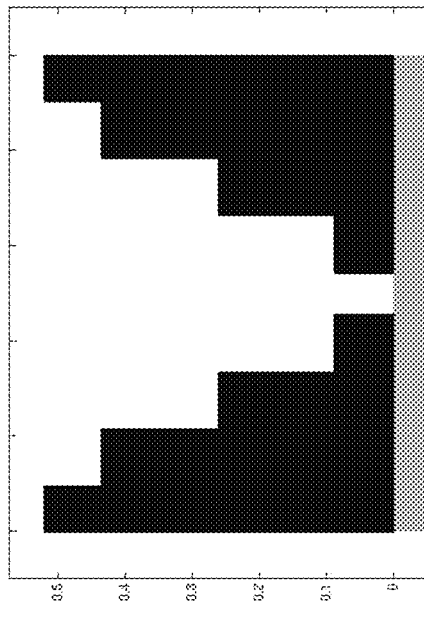
Figure 7D:
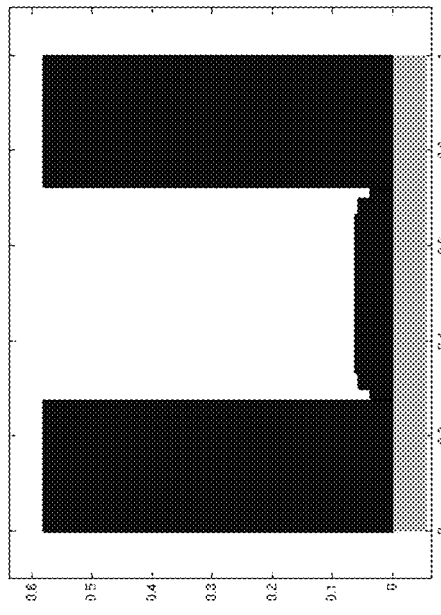

FIG. 7A and FIG. 7C indicate typical structures 711 and 712 merely by way of example, wherein FIG. 7B and FIG. 7D show the associated spectra 731 and 732 stored in a database. FIG. 6 indicates that individual auxiliary structures 621 on a wafer 601 can be optimized in each case for determining different parameters (e.g. overlay, layer thickness, CD value, etc.), wherein the corresponding identification of the relevant auxiliary structures can be effected in a database based manner (that is to say a prior input of the relevant information about the position of the auxiliary structures on the wafer is unnecessary).

Figure 9:
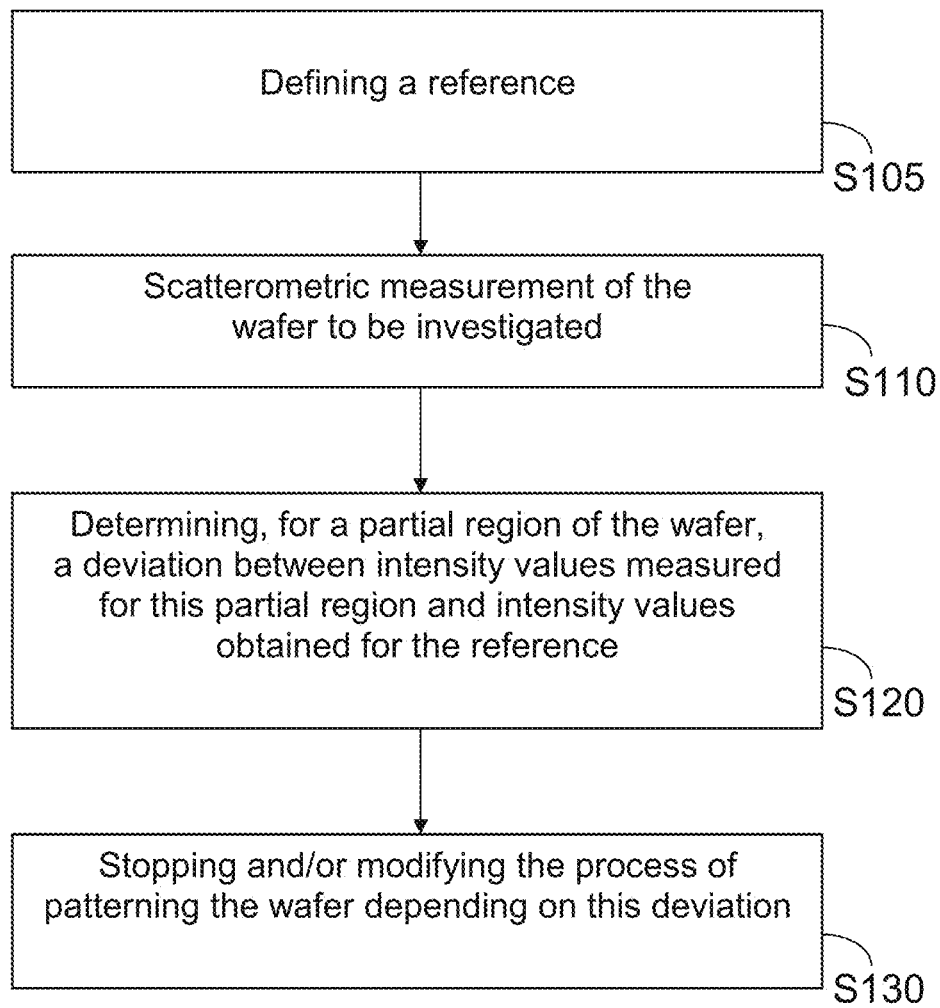
FIG. 9 shows a flow diagram for explaining the possible sequence of a further embodiment of a method according to the disclosure.

Further embodiments of the present disclosure are described below with reference to FIGS. 9 and 10, in which embodiments the outlay associated with creating a database in accordance with the embodiments described above is reduced or even completely avoided.

In accordance with this further aspect, on the basis of process variations occurring during the wafer patterning and on the basis of undesired changes in specific characteristic parameters (such as e.g. the etching depth) that accompany the process variations, it is deduced that the intensity values or spectra measured on a partial region of the wafer are compared with those of a reference. If this comparison reveals an "excessively high deviation" (for instance on account of a suitably predefined threshold value being exceeded), this can be used according to the disclosure automatically as a reason to interrupt, stop or modify the wafer patterning process.

The abovementioned partial regions of the wafer can be, in particular, partial regions outside the periodic (i.e. accessible to scatterometric measurements) used and auxiliary structures present on the wafer, wherein the disclosure makes use of the circumstance that the measurement data or intensity values present for these regions situated outside the used and auxiliary structures anyway (on account of the intensity measurement being effected simultaneously over a larger region) can likewise still be used expediently (for instance on account of still significant similarities to the marker regions). In accordance with FIG. 9, for this purpose, a step S105 involves firstly defining a suitable reference. The reference can be e.g. a wafer for which measurements already carried out on all marker regions have revealed a particularly good correspondence to the nominal values of the relevant characteristic parameters.

Step S110 involves carrying out in turn, in the customary manner according to the disclosure, the scatterometric measurement of the wafer to be examined in the form of an implementation of the intensity measurements for respectively different combinations of wavelength, polarization and/or order of diffraction, wherein here in particular measurement data are also determined for a partial region of the wafer that is situated outside the periodic used and marker structures.

A subsequent step S120 involves determining, for the relevant partial region of the wafer, the deviation between the intensity values measured there and the intensity values obtained for the reference in the corresponding region. Step S130 involves stopping and/or modifying the patterning process depending on the deviation (for instance if the deviation exceeds a suitably chosen threshold value). In the event of a threshold value being exceeded in this way, e.g. a corresponding alarm can then be triggered, whereupon correction measures are implemented in the chip fabrication process in order that the relevant spectrum is brought to correspondence again as much as possible with the spectrum obtained for the reference.

Figure 10:
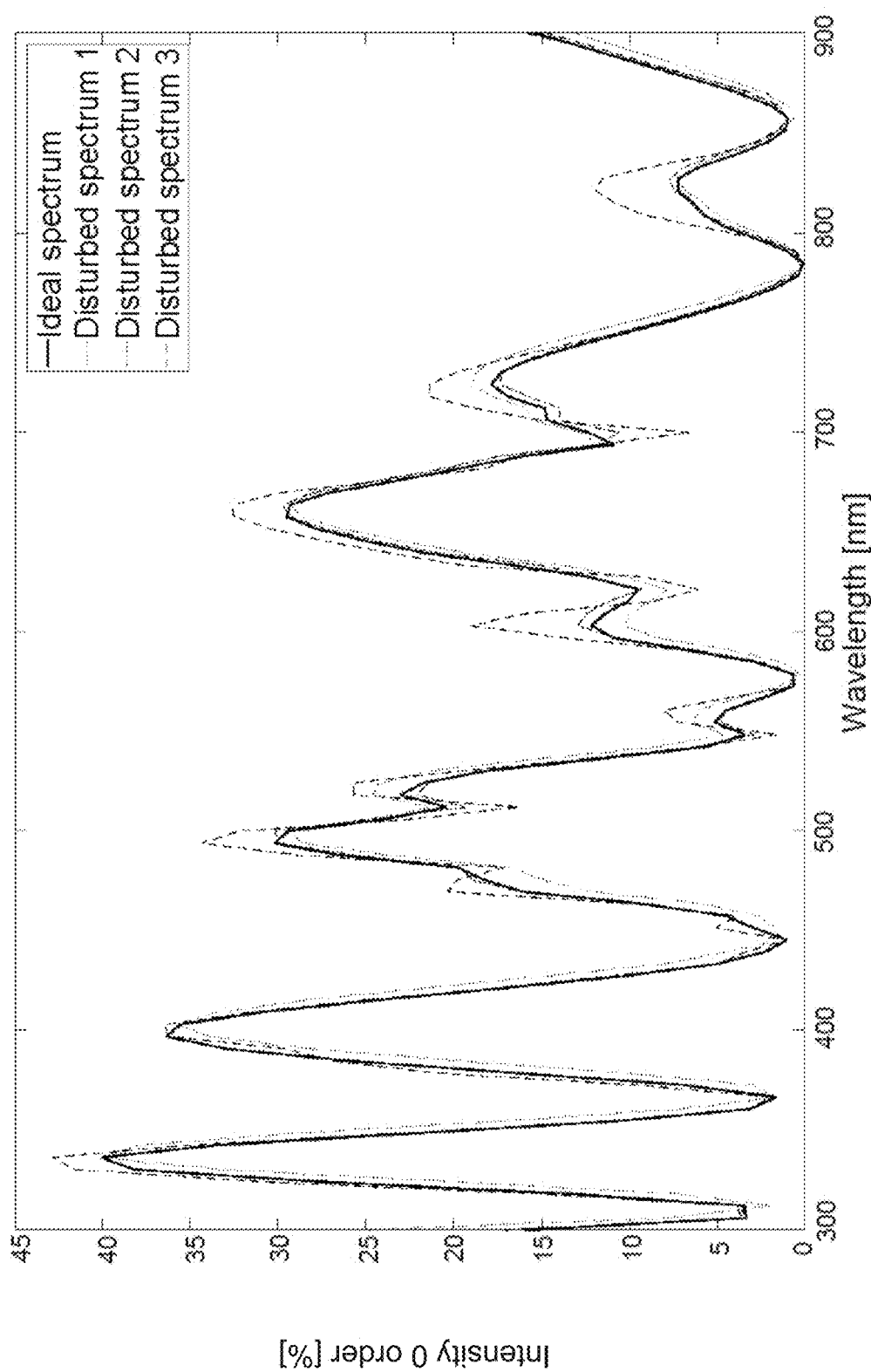
FIG. 10 shows a schematic illustration of exemplary possible spectra which are obtained in the method in accordance with the embodiment from FIG. 9 for spots having an identical structure on different wafers or chips in the case of slight process variations during the patterning.

In this respect, FIG. 10 shows a merely schematic illustration of different spectra for different wafers or chips which are subjected to fabrication processes that deviate slightly from one another in order to produce fundamentally identical structures.

In the visible wavelength range of between 400 nm and 700 nm, clearly significant deviations between the spectra are discernible, which indicate corresponding process variations and, in accordance with the embodiment described above, can be taken as a reason for an alarm or for the implementation of corresponding correction measures.

The definition of the corresponding threshold values which, when exceeded, cause an alarm to be triggered or correction measures in the wafer patterning process to be triggered can be effected in various ways. In this case, the respective threshold values or the tolerance band considered still to be permissible should be chosen with a magnitude such that measurement noise that occurs is always still tolerated. Specifically, the respective tolerance limits can be defined by a procedure in which firstly two wafers that are as far as possible identical are patterned, and in the process one of the wafers is altered in a targeted manner with regard to the relevant characteristic parameters (which can be ascertained via other suitable methods such as e.g. AFM), wherein a comparison of the spectra respectively obtained for these two wafers can then be carried out and used as a basis for the threshold value or tolerance band definition.

The method described above with reference to FIG. 9 and FIG. 10 can also be combined in any suitable way with the embodiments described above, wherein, for instance, in individual regions of the wafer to be examined, a database based determination of relevant characteristic parameters is effected and, in other partial regions of the wafer, without access to any databases, the automatic identification of process variations is effected on the basis of the comparison with a reference as described above with reference to FIG. 9 and FIG. 10.

Even though the disclosure has been described on the basis of specific embodiments, numerous variations and alternative embodiments are apparent to a person skilled in the art, for example by combination and/or exchange of features of individual embodiments. Accordingly, it goes without saying for the person skilled in the art that such variations and alternative embodiments are concomitantly encompassed by the present disclosure, and the scope of the disclosure is restricted only within the meaning of the appended patent claims and the equivalents thereof.

What is claimed is:

1. A method, comprising:
a) simultaneously performing intensity measurements of electromagnetic radiation diffracted at a used structure of a patterned wafer and at a plurality of auxiliary structures of the patterned wafer, wherein:
the intensity measurements of the electromagnetic radiation diffracted at the used structure of the patterned wafer are performed for at least one member selected from the group consisting of a wavelength of the electromagnetic radiation diffracted at the used structure of the patterned wafer, a polarization of the electromagnetic radiation diffracted at the used structure of the patterned wafer, and an order of diffraction of the electromagnetic radiation diffracted at the used structure of the patterned wafer; and
the measured intensity of the electromagnetic radiation diffracted at the plurality of auxiliary structures of the patterned wafer are performed for at least one member selected from the group consisting of a wavelength of the electromagnetic radiation diffracted at the plurality of auxiliary structures of the patterned wafer, a polarization of the electromagnetic radiation diffracted at the plurality of auxiliary structures of the patterned wafer, and an order of diffraction of the electromagnetic radiation diffracted at the plurality of auxiliary structures of the patterned wafer; and
b) determining a plurality of parameters characteristic of the patterned wafer based on:
i) the intensity measurements of the electromagnetic radiation diffracted at the used structure of the patterned wafer and at the plurality of auxiliary structures of the patterned wafer; and
ii) correspondingly calculated intensity values via a mathematical optimization method,
wherein determining the parameters characteristic of the patterned wafer comprises:
determining parameters of a first parameter set based on the measured intensity values for the electromagnetic radiation diffracted from the plurality of auxiliary structures; and
determining parameters of a second parameter set taking account of the parameters of the first parameter set.

2. The method of claim 1, wherein determining the parameters of the second parameter set comprises predefining the parameters of the first parameter set determined within a predefined variation interval.

3. The method of claim 2, wherein the plurality of auxiliary structures are configured based on a sensitivity analysis in which the sensitivity of different auxiliary structures is assessed for a diffraction-based determination of a respective one of the parameters of the first parameter set.

4. The method of claim 1, wherein the plurality of auxiliary structures are configured based on a sensitivity analysis in which the sensitivity of different auxiliary structures is assessed for a diffraction-based determination of a respective one of the parameters of the first parameter set.

5. The method of claim 1, wherein determining the parameters of the first parameter set on the basis comprises a comparison of the intensity values with intensity values stored in a database, and wherein in the database an associated intensity spectrum is respectively assigned to the plurality of auxiliary structures.

6. The method of claim 5, wherein a localization of structures respectively suitable for determining a parameter on the patterned wafer is effected based on the comparison with intensity values stored in the at least one database.

7. The method of claim 1, wherein the parameters characteristic of the patterned wafer comprise at least one parameter selected from the group consisting of a CD value, etching depth, and overlay accuracy of two structures produced in different lithography steps.

8. The method of claim 1, further comprising, for a partial region of the patterned wafer, comparing the measured intensity values for the partial region with intensity values obtained for a reference.

9. The method of claim 8, further comprising stopping or modifying the patterned wafer patterning process depending on the result of the comparison.

10. The method of claim 8, wherein the partial region of the patterned wafer is situated outside periodic used and auxiliary structures present on the patterned wafer.

11. The method of claim 8, wherein the partial region of the wafer is arranged adjacent to a used or auxiliary structure present on the patterned wafer.

12. A method, comprising:
a) simultaneously performing intensity measurements of electromagnetic radiation diffracted at a used structure of a patterned wafer and at an auxiliary structure of the patterned wafer, wherein:
the intensity measurements of the electromagnetic radiation diffracted at the used structure of the patterned wafer are performed for at least one member selected from the group consisting of a wavelength of the electromagnetic radiation diffracted at the used structure of the patterned wafer, a polarization of the electromagnetic radiation diffracted at the used structure of the patterned wafer, and an order of diffraction of the electromagnetic radiation diffracted at the used structure of the patterned wafer; and
the measured intensity of the electromagnetic radiation diffracted at the auxiliary structure of the patterned wafer are performed for at least one member selected from the group consisting of a wavelength of the electromagnetic radiation diffracted at the auxiliary structure of the patterned wafer, a polarization of the electromagnetic radiation diffracted at the auxiliary structure of the patterned wafer, and an order of diffraction of the electromagnetic radiation diffracted at the auxiliary structure of the patterned wafer; and
b) determining a plurality of parameters characteristic of the patterned wafer based on:
i) the intensity measurements of the electromagnetic radiation diffracted at the used structure of the patterned wafer and at the auxiliary structure of the patterned wafer; and
ii) correspondingly calculated intensity values via a mathematical optimization method,
wherein determining the parameters characteristic of the patterned wafer comprises:
determining parameters of a first parameter set based on the measured intensity values for the electromagnetic radiation diffracted from the auxiliary structure; and
determining parameters of a second parameter set taking account of the parameters of the first parameter set, and
wherein:
determining the parameters of the second parameter set comprises predefining the parameters of the first parameter set determined within a predefined variation interval; and
the auxiliary structure is configured based on a sensitivity analysis in which the sensitivity of different auxiliary structures is assessed for a diffraction-based determination of a respective one of the parameters of the first parameter set.

13. The method of claim 12, wherein the parameters characteristic of the patterned wafer comprise at least one parameter selected from the group consisting of a CD value, etching depth, and overlay accuracy of two structures produced in different lithography steps.

14. A method, comprising:
a) simultaneously performing intensity measurements of electromagnetic radiation diffracted at a used structure of a patterned wafer and at an auxiliary structure of the patterned wafer, wherein:
the intensity measurements of the electromagnetic radiation diffracted at the used structure of the patterned wafer are performed for at least one member selected from the group consisting of a wavelength of the electromagnetic radiation diffracted at the used structure of the patterned wafer, a polarization of the electromagnetic radiation diffracted at the used structure of the patterned wafer, and an order of diffraction of the electromagnetic radiation diffracted at the used structure of the patterned wafer; and
the measured intensity of the electromagnetic radiation diffracted at the auxiliary structure of the patterned wafer are performed for at least one member selected from the group consisting of a wavelength of the electromagnetic radiation diffracted at the auxiliary structure of the patterned wafer, a polarization of the electromagnetic radiation diffracted at the auxiliary structure of the patterned wafer, and an order of diffraction of the electromagnetic radiation diffracted at the auxiliary structure of the patterned wafer; and
b) determining a plurality of parameters characteristic of the patterned wafer based on:
i) the intensity measurements of the electromagnetic radiation diffracted at the used structure of the patterned wafer and at the auxiliary structure of the patterned wafer; and
ii) correspondingly calculated intensity values via a mathematical optimization method,
wherein determining the parameters characteristic of the patterned wafer comprises:
determining parameters of a first parameter set based on the measured intensity values for the electromagnetic radiation diffracted from the auxiliary structure; and
determining parameters of a second parameter set taking account of the parameters of the first parameter set, and
wherein the method further comprises, for a partial region of the patterned wafer, comparing the measured intensity values for the partial region with intensity values obtained for a reference.

15. The method of claim 14, further comprising stopping or modifying the patterned wafer patterning process depending on the result of the comparison.

16. The method of claim 14, wherein the partial region of the patterned wafer is situated outside periodic used and auxiliary structures present on the patterned wafer.

17. The method of claim 14, wherein the partial region of the wafer is arranged adjacent to a used or auxiliary structure present on the patterned wafer.

18. The method of claim 14, wherein determining the parameters of the second parameter set comprises predefining the parameters of the first parameter set determined within a predefined variation interval.

19. The method of claim 14, wherein the auxiliary structure is configured based on a sensitivity analysis in which the sensitivity of different auxiliary structures is assessed for a diffraction-based determination of a respective one of the parameters of the first parameter set.

20. The method of claim 14, wherein the parameters characteristic of the patterned wafer comprise at least one parameter selected from the group consisting of a CD value, etching depth, and overlay accuracy of two structures produced in different lithography steps.

* * * * *

UNITED STATES PATENT AND TRADEMARK OFFICE
CERTIFICATE OF CORRECTION

PATENT NO. : 10,509,330 B2
APPLICATION NO. : 15/918187
DATED : December 17, 2019
INVENTOR(S) : Hans-Michael Stiepan, Andy Zott and Ulrich Mantz Page 1 of 1

It is certified that error appears in the above-identified patent and that said Letters Patent is hereby corrected as shown below:

In the Specification

Column 1, Line 16, delete "herein" and insert -- herein. --.

Signed and Sealed this
Twenty-first Day of April, 2020

Andrei Iancu
*Director of the United States Patent and Trademark Office*